United States Patent [19]

Reiter et al.

[11] Patent Number: 5,135,928
[45] Date of Patent: Aug. 4, 1992

[54] TRIAZOLO DERIVATIVES AND PROCESS FOR THEIR PREPARATION

[75] Inventors: József Reiter; József Barkóczy; Lujza Petócz; Frigyes Görgényi; Márton Fekete; Enikó Szirt née Kiszelly; Gábor Gigler; István Gacsályi; István Gyertyán; Klára Reiter née Esses, all of Budapest, Hungary

[73] Assignee: Egis Gyógyszergy',acu/a/ r, Budapest, Hungary

[21] Appl. No.: 604,486

[22] Filed: Oct. 25, 1990

[30] Foreign Application Priority Data

Oct. 25, 1989 [HU] Hungary .................. 5427/89
Oct. 25, 1989 [HU] Hungary .................. 5429/89

[51] Int. Cl.[5] ............. C07D 487/04; C07D 249/14; A61K 31/55; A61K 31/41
[52] U.S. Cl. .................. 514/233.2; 514/236.2; 514/252; 514/254; 514/388; 514/384; 540/501; 544/132; 544/366; 548/263.8; 548/265.2
[58] Field of Search .......... 540/501; 548/263.8, 548/265.2; 544/132, 366; 514/233.2, 236.2, 252, 254, 383, 384

[56] References Cited

U.S. PATENT DOCUMENTS 4,144,233 3/1979 Britton .................. 540/501

Primary Examiner—Robert Gerstl
Attorney, Agent, or Firm—Beveridge, DeGrandi & Weilacher

[57] ABSTRACT

This invention relates to novel triazolo derivatives, a process for the preparation thereof, pharmaceutical compositions comprising the same, to the use of the said triazolo derivatives for the treatment of diseases and also for the preparation of pharmaceutical compositions suitable for the treatment of the said diseases.

The new triazolo derivatives of the general formulae (Ia) and (Ib),

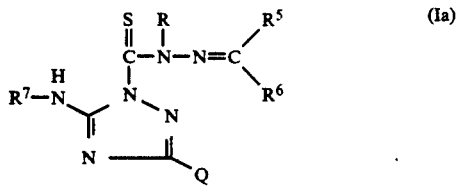

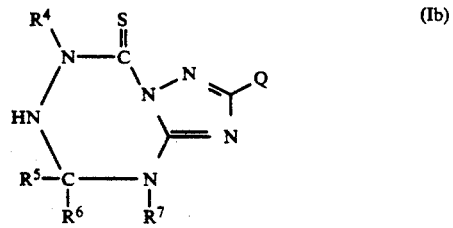

wherein

Q represents hydrogen or a heterocyclic group optionally bearing one or more $C_{1-4}$ alkyl substituent(s); or a group of the formula $SR^1$, wherein $R^1$ stands for straight or branched chained $C_{1-4}$ alkyl or phenyl-($C_{1-4}$ alkyl); or q represents a group of the formula $NR^2R^3$, wherein
$R^2$ and $R^3$ each represent hydrogen, straight or branched chain $C_{1-12}$ alkyl, $C_{2-6}$ alkenyl or phenyl-($C_{1-4}$ alkyl);
$R^4$ and $R^7$ each represent hydrogen, $C_{1-6}$ alkyl or phenyl-($C_{1-4}$ alkyl) optionally bearing one or more halogen substituent(s);
$R^5$ and $R^6$ each stand for $C_{1-4}$ alkyl optionally substituted by a $C_{1-4}$ alkoxycarbonyl group; a heterocyclic group or a phenyl group optionally bearing one or more halogen, hydroxyl, cyano, nitro, alkyl, methylene dioxy and carbamoylmethoxy, di-($C_{1-4}$ alkyl)-amino or $C_{1-4}$ alkoxy substituent(s) which latter may carry a di-($C_{1-4}$ alkyl)-amino group; furthermore one of $R^5$ and $R^6$ may represent hydrogen, or
$R^5$ and $R^6$ together stand for $C_{4-15}$ alkylene, or together with the adjacent carbon atom they are attached to form a heterocyclic group bearing a phenyl($C_{1-4}$ alkyl) substituent, possess valuable antianginal and tranquillant/sedative properties and are useful in therapy.

5 Claims, No Drawings

TRIAZOLO DERIVATIVES AND PROCESS FOR THEIR PREPARATION

This invention relates to novel triazolo derivatives, a process for the preparation thereof, pharmaceutical compositions comprising the same, the use of the said triazolo derivatives for the treatment of diseases and also for the preparation of pharmaceutical compositions suitable for the treatment of the said diseases.

According to an aspect of the present invention there are provided new triazolo derivatives of the general formulae (Ia) and (IB),

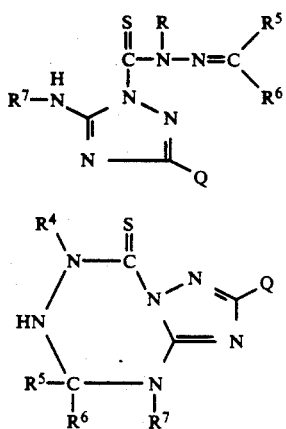

mixtures and pharmaceutically acceptable salts thereof, wherein

Q represents hydrogen or a heterocyclic group optionally bearing one or more $C_{1-4}$ alkyl substituent(s); or a group of the formula $SR^1$, wherein $R^1$ stands for straight or branched chained $C_{1-4}$ alkyl or phenyl-($C_{1-4}$ alkyl); or Q represents a group of the formula $NR^2R^3$, wherein $R^2$ and $R^3$ each represent hydrogen, straight or branched chain $C_{1-12}$ alkyl, $C_{2-6}$ alkenyl or phenyl-($C_{1-4}$ alkyl);

$R^4$ and $R^7$ each represent hydrogen, $C_{1-6}$ alkyl or phenyl-($C_{1-4}$ alkyl) optionally bearing one or more halogen substituent(s);

$R^5$ and $R^6$ each stand for $C_{1-4}$ alkyl optionally substituted by a $C_{1-4}$ alkoxycarbonyl group; a heterocyclic group of a phenyl group optionally bearing one or more halogen, hydroxyl, cyano, nitro, alkyl, methylene dioxy and carbamoylmethoxy, di-($C_{1-4}$ alkyl)-amino or $C_{1-4}$ alkoxy substituent(s) which latter may carry a di-($C_{1-4}$ alkyl)-amino group; furthermore one of $R^5$ and $R^6$ may represent hydrogen, or $R^5$ and $R^6$ together stand for $C_{4-15}$ alkylene, or together with the adjacent carbon atom they are attached to form a heterocyclic group bearing a phenyl-($C_{1-4}$ alkyl) substituent.

The compounds of the general formulae (Ia) and (Ib) are ring-chain tautomers, thus in solution—depending on the quality and temperature of the solvent—they can be converted into one another.

The invention encompasses all of the other isomers or tautomeric forms of the compounds of the general formulae (Ia) and (Ib), too.

The compounds according to the present invention exhibit excellent biological activity and low toxicity, e.g. they possess tranquillant/sedative, antianginal, analgesic, antiinflammatory, gastric-secretion inhibiting, gastric-ulcer inhibiting and/or antiperistaltic effects, furthermore they can be used as starting materials for the preparation of other pharmaceutically active derivatives as well.

The term "heterocyclic group" used throughout the specification relates to 4 to 8 membered heterocyclic groups which can be formed from compounds comprising independently one or more nitrogen and/or oxygen atom(s) or a group which can be obtained by condensing the same compounds with each other or with benzene. Such groups may be aromatic or partially or completely saturated and may be substituted by one or more substituent(s).

As examples for such groups e.g. the piperidyl, morpholinyl, piperazinyl, furyl, imidazolyl, pyridyl, pyrimidinyl, pyrrolyl, pyrazolyl, pyridazinyl, isoxazolyl, pyrrolinyl, pyrrolidinyl, imidazolidinyl, imidazolinyl, pyrazolidinyl, pyrazolinyl, pyranyl or delta-3-piperidin-1-yl groups are mentioned.

The term "alkyl group" means a straight or branched chained saturated aliphatic hydrocarbon group comprising 1 to 4, 1 to 6 or 1 to 12 carbon atom(s), e.g. methyl, ethyl, octyl, il-butyl, tert.butyl, dodecyl groups. The term "alkoxy group" relates to alkyl ether groups comprising alkyl groups having 1 to 4 carbon atom(s), e.g. methoxy, ethoxy, tert.butoxy etc. groups. As "$C_{2-6}$ alkenyl" groups straight or branched chained alkenyl groups are mentioned (e.g. vinyl, allyl, 2-methyl-allyl, 1-propenyl, 2-propenyl, 1-butenyl, 2-butenyl, 2-pentenyl, 2-hexenyl etc.). The "phenyl-($C_{1-4}$ alkyl) groups comprise alkyl groups having 1 to 4 carbon atoms (e.g. benzyl, 1-phenyl-ethyl, 2-phenylethyl, 4-phenyl-butyl etc.). The "$C_{1-4}$ alkoxycarbonyl" group may be e.g. methoxycarbonyl, ethoxycarbonyl, butoxycarbonyl etc. The term "di-($C_{1-4}$ alkyl)-amino relates to groups such as dimethylamino, diethylamino, di-n-propylamino, di-tert.butylamino etc.

Compounds of the general formulae (Ia) and (Ib), wherein Q represents morpholino, $R^4$ stands for $C_{1-4}$ alkyl, $R^5$ and $R^6$ denote phenyl bearing one or more halogen substituent(s) or together stand for $C_{4-15}$ alkylene, and pharmaceutically acceptable acid addition salts thereof possess particularly valuable pharmaceutical properties.

Particularly preferred representatives of the compounds of the general formulae (Ia) and (Ib) are the following derivatives:

1-(5-amino-3-morpholino-1H-1,2,4-triazol-1-yl)-N-methyl-N'-(2,6-dichlorobenzylidene)carbothiohydrazide, 6-methyl-2-morpholino-5,6,8,9-tetrahydro[1,2,4]-triazolo-]1,4-d]-[1,2,4,6]tetrazepin-5(7H)-thione-8-spiro-1'-cyclododecane, 6-methyl-2-morpholino-5,6,8,9-tetrahydro[1,2,4]-triazolo-[1,5-d]-[1,2,4,6]tetrazepin-5(7H)-thione-8-spiro-1'-cyclopentane, and pharmaceutically acceptable acid addition salts thereof.

The compounds of the general formulae (Ia) and (Ib) are organic bases, so they can be transformed into acid addition salts. The pharmaceutically acceptable acid addition salts of the compounds of the general formulae (Ia) and (Ib) can be formed with inorganic or organic acids. As examples for the pharmaceutically acceptable acid addition salts the hydrohalides (such as hydrochlorides or hydrobromides), carbonates, sulfates, acetates, fumarates, maleates, citrates, ascorbinates and tartarates can be mentioned.

According to a further aspect of the present invention there is provided a process for the preparation of the compounds of the general formulae (Ia) and (Ib), mixtures and pharmaceutically acceptable acid addition salts thereof, which comprises reacting a triazolyl hydrazide of the general formula (II),

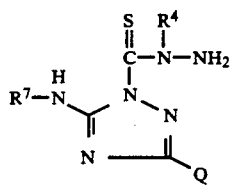 (II)

wherein Q, $R^4$ and $R^7$ are as stated above, with an oxo compound of the general formula (III),

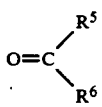 (III)

wherein $R^5$ and $R^6$ are as stated above,
then, if desired, separating the ring-chain tautomers of the general formulae (Ia) and (Ib) thus obtained from each other or, if desired, subjecting a compound of the general formula (Ia) to cyclization.

The reaction of the compounds of the general formulae (II) and (III) is carried out in a solvent inert toward the reactants. For this purpose preferably polar or apolar solvents, such as $C_{1-4}$ alcohols (e.g. methanol or 2-propanol) or dimethylformamide are used. An excess of the oxo compound of the general formula (II) may also serve as solvent.

The reaction is performed at a temperature between 0° C. and 200° C. For the preparation of compounds of the general formula (Ia) it is preferable to work at a temperature of 20 to 80° C., while for the preparation of compounds of the general formula (Ib) the reaction is preferably carried out between 80° C. and 160° C.

The cyclization of the triazolo derivatives of the general formula (Ia) into compounds of the general formula (Ib) is carried out in an inert solvent. For this purpose polar or apolar solvents such as an aqueous dimethylformamide solution or acetic acid can be used. This reaction is carried out at a temperature between 40° C. and 200° C., preferably between 80° C. and 160° C.

The compounds of the general formulae (Ia) and (Ib) obtained in form of bases can be converted into acid addition salts by methods known per se. For this purpose the free bases are reacted with the corresponding acid in an inert solvent.

The starting materials of the synthesis according to the invention, namely the compounds of the general formula (II), are prepared by reacting a triazolyl-dithio ester of the general formula (IV),

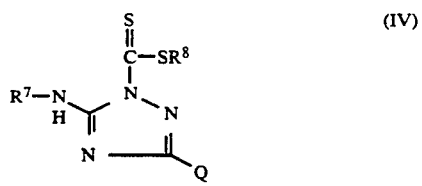 (IV)

wherein $R^7$ is as stated above and $R^8$ represents $C_{1-4}$ alkyl or phenyl optionally substituted by one or more halogen atom(s), with a hydrazine derivative of the general formula (V),

 (V)

wherein $R^4$ is as stated above, preferably in methanol or isopropanol, at a temperature of 20° to 110° C.

The triazolyl-dithio esters of the general formula (IV) are known compounds or can be prepared on the analogy of the known derivatives (U.S. Pat. No. 3,686,301; DD patent specification No. 105,897).

The hydrazine derivatives of the general formula (V) are also known compounds (Beilsteins Handbuch der Organischen Chemie 4, 546, Verlag Springer, Berlin, 1922; Ullmann: Encyklopädie der Technischen Chemie 13, 95, Verlag Chemie, Weinheim, 1977).

The compounds of the general formulae (Ia) and (Ib) are very slightly toxic and show excellent biological properties. They possess transquillant/sedative, antianginal, analgesic, antiinflammatory, gastric-secretion inhibiting, gastric-ulcer inhibiting and/or antiperistaltic effects.

The activity of the compounds of the general formulae (Ia) and (Ib) is shown by the following tests.

1. Hexobarbital narcosis on mice

Method: Kaergaard, Arch. Int. Pharmacodyn. 2, 170, (1967)

Groups consisting of 6 mice are used for each dose. The animals are treated orally with the test compound (the control group receives a vehicle), whereby sleeping is induced 1 hour later by administering a 40 mg/kg i.v. dose of Hexobarbital both to the test and control groups.

Evaluation

Animals which have a sleeping time more than 2.5 times longer than that of the control group are considered to show a positive reaction. $ED_{50}$ values are calculated from the thus-transformed data. The results are summarized in Table I.

TABLE I

| Hexobarbital narcosis on mice | | |
|---|---|---|
| Test compound (Example No.) | $ED_{50}$ mg/kg | Therapeutical index |
| 7 | 110 | 9.1 |
| 22 | 110 | 5.1 |
| 5 | 36 | 27.8 |
| 53 | 41 | 48.8 |
| 41 | 200 | 10.0 |
| 47 | 200 | 10.0 |
| 58 | 160 | 12.5 |
| Meprobamate | 270 | 4.1 |

The above data show that the compounds of the general formula (Ia) and (Ib) are superior to the reference substance Meprobamate regarding both the absolute dose and the therapeutical index.

2. Antianginal effect

Method: Nieschultz, E., Popendiker, K. and Hoffmann, I.: Arzneimittel Forschung 5, 680 (1955)

Male rats of 180–220 g body weight were narcotised with chloralese-urethane (70/700 mg/kg ip.). The ECG was registered with needle electrodes in standard II leading. The experimental coronaria insufficiency was induced with vasopressin (4 NE/kg i.v.). The height of wave T in ECG was measured before and after the administration of vasopressin in both the control and treated groups. Test compounds were administered intravenously 2 minutes prior to the treatment with vasopressin. The results are summarized in Table II.

TABLE II

| Antianginal effect | |
|---|---|
| Test compound Example No. | $ED_{50}$ mg/kg i.v. |
| 48 | 1.35 |
| 53 | 1.0 |
| 57 | 1.65 |
| Prenylamine | 6.5 |

The above data show that certain representatives of the compounds of the general formula (Ib) are 4 to 7 times more effective on the antianginal test than the reference substance Prenylamine.

According to a further aspect of the present invention there are provided pharmaceutical compositions comprising as active ingredient at least one compound of the general formula (Ia) or (Ib) in admixture with suitable insert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatine capsule, solution, emulsion or suspension), parenteral (e.g. injection solution) or rectal (e.g. suppository) administration.

As carrier for the preparation of tablets, coated tablets, dragées and solid gelatine capsules e.g. lactose, corn starch, potatoe starch, talc, magnesium carbonate, magnesium stearate, calcium carbonate, stearic acid, etc. or the salts thereof can be used. As carrier for the soft gelatine capsules e.g. vegetable oils, fats, waxes or polyols of suitable consistency can be used. As carriers for the solutions and syrups e.g. water, polyols (polyethylene glycol), saccharose or glucose can be used. The injection solutions can comprise e.g. water, alcohols, polyols, glycerol or vegetable oils as carrier. The suppositories can be prepared with the aid of e.g. oils waxes, fats or polyols of suitable consistency.

In addition, the pharmaceutical formulations may comprise auxiliary agents usually applied in the pharmaceutical industry, e.g. wetting, sweetening agents, aroma substances, salts causing the change of osmotic pressure, buffers, etc. The pharmaceutical formulations may further comprise other active ingredients together with the compounds of the general formulae (Ia) or (Ib).

The compounds of the general formulae (Ia) and (Ib) can preferably be used in therapy orally in the form of tablets or capsules. Especially preferred are the capsules or tablets comprising about 250 mg of active ingredient.

The daily dose of the compounds of the general formulae (Ia) and (Ib) can vary within wide ranges depending on several factors, e.g. on the activity of the active ingredient, the patient's condition and age, the severity of the disease, etc. The oral dose is generally 10 to 10,000 mg/day, preferably 100 to 1000 mg/day. It has to be stressed that the above doses are only of informative character and the administered dose must always be determined by the physician therapeutist.

According to a further aspect of the present invention there is provided the use of the compounds of the general formulae (Ia) and (Ib) and mixtures or pharmaceutically acceptable salts thereof for the preparation of pharmaceutical compositions having particularly tranquillant/sedative and/or antianginal effects.

According to a still further aspect of the present invention there is provided a method of tranquillant/sedative and/or antianginal treatment which comprises administering to the patient an effective amount of a compound of the general formula (Ia) and/or (Ib).

Further details of the present invention are to be found in the following Examples without limiting the scope of protection to the said Examples.

EXAMPLE 1

1-(5-Amino-3-morpholino-1H-1,2,4-triazol-1-yl)-N-methyl-N'-(4-nitrobenzylidene)carbothiohydrazide 2.55 g (0.01 mole) of 1-(5-amino-3-morpholino-1H-1,2,4-triazol-1-yl)-N-methyl-carbothiohydrazide are boiled in 25 ml of ethanol, in the presence of 1.81 g (0.012 mole) of 4-nitrobenzaldehyde for 2 hours. The reaction mixture is then cooled, the separated crystals are filtered off and recrystallized from acetnitrile.

Yield: 3.04 g (78%).

M.p.: 218° to 220° C.

EXAMPLE 2

1-(5-Amino-3-morpholino-1H-1,2,4-triazol-1-yl)-N-methyl-N'-(3-nitrobenzylidene)carbothiohydrazide 2.55 g (0.01 mole) of 1-(5-amino-3-morpholino-1H-1,2,4-triazol-1-yl)-N-methyl-carbothiohydrazide are boiled in 25 ml of ethanol, in the presence of 1.81 g (0.012 mole) of 3-nitrobenzaldehyde for 3 hours. The reaction mixture is then cooled, the separated crystals are filtered off and recrystallized from acetonitrile.

Yield: 3.28 g (84%).

M.p.: 198° to 200° C.

EXAMPLE 3

1-(5-Amino-3-morpholino-1H-1,2,4-triazol-1-yl)-N-methyl-N'-(4-cyanobenzylidene)carbothiohydrazide 2.55 g (0.01 mole) of 1-(5-amino-3-morpholino-1H-1,2,4-triazol-1-yl)-N-methyl-carbothiohydrazide are boiled in 25 ml of ethanol, in the presence of 1.57 g (0.012 mole) of 4-cyanobenzaldehyde for 2 hours. The reaction mixture is then cooled, the separated crystals are filtered off and recrystallized from acetonitrile.

Yield: 2.68 g (72%).

M.p.: 240° to 242° C.

EXAMPLE 4

1-(5-Amino-3-morpholino-1H-1,2,4-triazol-1-yl)-N-methyl-N'-(4-chlorobenzylidene)carbothiohydrazide 2.55 g (0.02 mole) of 1-(5-amino-3-morpholino-1H-1,2,4-triazol-1-yl)-N-methyl-carbothiohydrazide are boiled in 25 ml of ethanol, in the presence of 1.69 g (0.012 mole) of 4-chlorobenzaldehyde for 3 hours. The reaction mixture is then cooled, the separated crystals are filtered off and recrystallized from acetonitrile.

Yield: 2.85 g (75%).
M.p.: 192° to 194° C.

EXAMPLE 5

1-(5-Amino-3-morpholino-1H-1,2,4-triazol-1-yl)-N-methyl-N'-(2,6-dichlorobenzylidene)carbothiohydrazide 2.55 g (0.001 mole) of 1-(5-amino-3-morpholino-1H-1,2,4-triazol-1-yl)-N-methyl-carbothiohydrazide are boiled in 25 ml of ethanol, in the presence of 2.1 g (0.012 mole) of 2,6-dichlorobenzaldehyde for 1 hour. The reaction mixture is then cooled, the separated crystals are filtered off and recrystallized from 2-propanol.

Yield: 3.44 g (83%).
M.p.: 152° to 154° C.

EXAMPLE 6

1-(5-Amino-3-morpholino-1H-1,2,4-triazol-1-yl)-N-methyl-N'-(3-hydroxybenzylidene)carbothiohydrazide 2.55 g (0.01 mole) of 1-(5-amino-3-morpholino-1H1,2,4-triazol-1-yl)-N-methyl-carbothiohydrazide are boiled in 25 ml of ethanol, in the presence of 1.47 g (0.012 mole) of 3-hydroxybenzaldehyde for 3 hours. The reaction mixture is then cooled, the separated crystals are filtered off and recrystallized from acetonitrile.

Yield: 2.49 g (69%).
M.p.: 187° to 189° C.

EXAMPLE 7

1-(5-Amino-3-morpholino-1H-1,2,4-triazol-1-yl)-N-methyl-N'-(4-carbamoylmethoxybenzylidene)carbothiohydrazide 2.55 g (0.01 mole) of 1-(5-amino-3--morpholino-1H-1,2,4-triazol-1-yl)-N-methyl-carbothiohydrazide are boiled in 25 ml of ethanol, in the presence of 2.14 g (0.012 mole) of 4-carbamoylmethoxybenzaldehyde for 5 hours. The reaction mixture is then cooled, the separated crystals are filtered off and recrystallized from dimethylformamide.

Yield: 3.64 g (87%).
M.p.: 236° to 238° C.

EXAMPLE 8

1-(5-Amino-3-morpholino-1H-1,2,4-triazol-1-yl)-N-methyl-N'-(3,4,5-triamethoxybenzylidene)carbothiohydrazide 2.55 g (0.01 mole) of 1-(5-amino-3-morpholino-1H-1,2,4-triazol-1-yl)-N-methyl-carbothiohydrazide are boiled in 25 ml of ethanol, in the presence of 2.35 g (0.012 mole) of 3,4,5-trimethoxybenzaldehyde for 4 hours. The reaction mixture is then cooled, the separated crystals are filtered off and recrystallized from acetonitrile.

Yield: 3.38 g (79%).
M.p.: 180° to 182° C.

EXAMPLE 9

1-(5-Amino-3-morpholino-1H-1,2,4-triazol-1-yl)-N-methyl-N'-benzylidenecarbothiohydrazide 2.55 g (0.01 mole) of 1-(5-amino-3-morpholino-1H-1,2,4-triazol-1-yl)-N-methyl-carbothiohydrazide are boiled in 25 ml of ethanol, in the presence of 1.22 ml (0.012 mole) of benzaldehyde for 4 hours. The reaction mixture is then cooled, the separated crystals are filtered off and recrystallized from 2-propanol.

Yield: 2.35 g (68%).
M.p.: 194° to 196° C.

EXAMPLE 10

1-(5-Amino-3-morpholino-1H-1,2,4-triazol-1-yl)-N-methyl-N'-(4-dimethylaminobenzylidene)carbothiohydrazide 2.55 g (0.01 mole) of 1-(5-amino-3-morpholino-1H-1,2,4-triazol-1-yl)-N-methyl-carbothiohydrazide are boiled in 25 ml of ethanol, in the presence of 1.79 g (0.012 mole) of 4-dimethylaminobenzaldehyde for 5 hours. The reaction mixture is then cooled, the separated crystals are filtered off and recrystallized from methanol.

Yield: 2.80 g (72%).
M.p.: 185° to 187° C.

EXAMPLE 11

1-(5-Amino-3-methylthio-1H-1,2,4-triazol-1yl)-N-methyl-N'-benzylidenecarbothiohydrazide 2.18 g (0.01 mole) of 1-(5-amino-3-methylthio-1H-1,2,4-triazol-1yl)-N-methyl-carbothiohydrazide are boiled in 25 ml of ethanol, in the presence of 1.22 ml (0.012 mole) of benzaldehyde for 4 hours. The reaction mixture is then cooled, the separated crystals are filtered off and recrystallized from methanol.

Yield: 2.20 g (72%).
M.p.: 185° to 187° C.

EXAMPLE 12

1-(5-Amino-3-methylthiol-1H-1,2,4-triazol-1-yl)-N-methyl-N'-(4-nitrobenzylidene)carbothiohydrazide 2.18 g (0.01 mole) of 1-(5-amino-3-methylthio-1H-1,2,4-triazol-1-yl)-N-methyl-carbothiohydrazide are boiled in 25 ml of ethanol, in the presene of 1.81 g (0.012 mole) of 4-nitrobenzaldehyde for 2 hours. The reaction mixture is then cooled, the separated crystals are filtered off and recrystallized from dioxane.

Yield: 2.57 (73%).
M.p.: 231° to 233° C.

EXAMPLE 13

1-(5-Amino-3-methylthio-1H-1,2,4-triazol-1-yl)-N-methyl-N'-(3-nitrobenzylidene)carbothiohydrazide 2.18 g (0.01 mole) of 1-(5-amino-3-methylthio-1H-1,2,4-triazol-1-yl)-N-methyl-carbothiohydrazide are boiled in 25 ml of ethanol, in the presence of 1.81 g (0.012 mole) of 3-nitrobenzaldehyde for 2 hours. The reaction mixture is then cooled, the separated crystals are filtered off and recrystallized from dioxane.

Yield: 2.88 g (82%).
M.p.: 214° to 216° C.

EXAMPLE 14

1-(5-Amino-3-methylthiol-1H-1,2,4-triazol-1yl)-N-methyl-N'-(4-cyanobenzylidene)carbothiohydrazide 2.18 g (00.01 mole) of 1-(5-amino-3-methylthio-1H-1,2,4-triazol-1-yl)-N-methyl-carbothiohydrazide are boiled in 25 ml of ethanol, in the presence of 1.57 g (0.012 mole) of 4-cyanobenzaldehyde for 3 hours. The reaction mixture is then cooled, the separated crystals are filtered off and recrystallized from acetonitrile.

Yield: 3.01 g (91%).
M.p.: 224° to 226° C.

EXAMPLE 15

1-(5-Amino-3-methylthiol-1-H-1,2,4-triazol-1-yl)-N-methyl-N'-(4-chlorobenzylidene)carbothiohydrazide 2.18 g (0.01 mole) of 1-(5-amino-3-methylthio-1H-1,2,4-triazol-1yl)-N-methyl-carbothiohydrazide are boiled in 25 ml of ethanol, in the presence of 1.69 g (0.012 mole) of 4-chlorobenzaldehyde for 3 hours. The reaction mixture is then cooled, the separated crystals are filtered off and recrystallized from dioxane.

Yield: 2.69 g (79%).
M.p.: 190° to 192° C.

EXAMPLE 16

1-(5-Amino-3-methylthio-1H-1,2,4-triazol-1-yl)-N-methyl-N'-(4-chlorobenzylidene)carbothiohydrazide 2.18 g (0.01 mole) of 1-(5-amino-3-methylthio-1-H-1,2,4-triazol-1-yl)-N-methyl-carbothiohydrazide are stirred in 25 ml of ethanol, in the presence of 1.69 g (0.012 mole) of 4-chlorobenzaldehyde for 8 hours at 50° C. The reaction mixture is then cooled, the separated crystals are filtered off and recrystallized from dioxane.

Yield: 2.62 g (77%).
M.p.: 190° to 192° C.

EXAMPLE 17

1-(5-Amino-3-methylthiol-1H-b 1,2,4-triazol-1-yl)-N-methyl-N'-(3-hydroxybenzylidene)carbothiohydrazide 2.18 g (0.01 mole) of 1-(5-amino-3-methylthiol-1H-1,2,4-triazol-1-yl)-N-methyl-carbothiohydrazide are boiled in 25 ml of ethanol, in the presence of 1.47 g (0.012 mole) of 3-hdyroxybenzaldehyde for 3 hours. The reaction mixture is then cooled, the separated crystals are filtered off and recrystallized from acetonitrile.

Yield: 2.68 g (83%).
M.p: 192° to 194° C.

EXAMPLE 18

1-(5-Amino-3-methylthio-1H-1,2,4-triazol-1-yl)-N-methyl-N'-(4-fluorobenzylidene)carbothiohydrazide 2.18 g (0.01 mole) of 1-(5-amino-3-methylthio-1-H-1,2,4-triazol-1-yl)-N-methyl-carbothiohydrazide re boiled in 25 ml of ethanol, in the presence of 1.29 ml (0.012 mole) of 4-fluorobenzaldehyde for 3 hours. The reaction mixture is then cooled, the separated crystals are filtered off and recrystallized from acetonitrile.

Yield: 3.02 g (93%).
M.p.: 209° to 211° C.

EXAMPLE 19

1-(5-Amino-3-methylthio-1H-1,2,4-triazol-1-yl)-N-methyl-N'-(4-dimethylaminobenzylidene)carbothiohydrazide 2.18 g (0.01 mole) of 1-(5-amino-3-methylthio-1H-1,2,4-triazol-1--yl)-N-methyl-carbothiohydrazide are boiled in 25 ml of ethanol, in the presence of 1.79 g (0.012 mole) of 4-dimethylaminobenzaldehyde for 5 hours. The reaction mixture is then cooled, the separated crystals are filtered off and recrystallized from dioxane.

Yield: 3.00 g (86%).
M.p.: 168° to 170° C.

EXAMPLE 20

1-(5-Amino-3-methylthiol-1H-1,2,4-triazol-1-yl)-N-methyl-N'-(4-carbamoylmethoxybenzylidene)carbothiohydrazide 2.18 g (0.01 mole) of 1-(5-amino-3-methylthio-1H-1,2,4-triazol-1-yl)N-methyl-carbothiohydrazide re boiled in 25 ml of ethanol, in the presence of 2.14 g (0.012 mole) of 4-carbamoylmethoxybenzaldehyde for 5 hours. The reaction mixture is then cooled, the separated crystals are filtered off and recrystallized from methanol.

Yield: 3.14 g (86%).
M.p.: 188° to 190° C.

EXAMPLE 21

1-(5-Amino-3-methylthio-1H-1,2,4-triazol-1-yl)-N-methyl-N'-(3,4,5-trimethoxybenzylidene)carbothiohydrazide 2.18 g (0.01 mole) of 1-(5-amino-3-methylthio-1H-1,2,4-triazol-1yl)-N-methyl-carbothiohydrazide are boiled in 25 ml of ethanol, in the presence of 2.35 g (0.012 mole) of 3,4,5-trimethoxybenzaldehyde for 4 hours. The reaction mixture is then cooled, the separated crystals are filtered off and recrystallized from dioxane.

Yield: 3.6 g (91%).
M.p.: 229° to 231° C.

EXAMPLE 22

1-(5-Amino-3-methylthio-1H-1,2,4-triazol-1-yl)-N-methyl-N'-(4-hydroxy-3-methoxybenzylidene)carbothiohydrazide 2.18 g (0.01 mole) of 1-(5-amino-3-methylthio-1H-1,2,4-triazol-1-yl)-N-methyl-carbothiohydrazide are boiled in 25 ml of ethanol, in the presence of 1.83 g (0.012 mole) of 4-hydroxy-3-methoxybenzaldehyde for 5 hours. The reaction mixture is then cooled, the separated crystals are filtered off and recrystallized from methanol.

Yield: 2.50 g (71%).
M.p.: 214° to 216° C.

EXAMPLE 23

1-(5-Amino-3-methylthio-1H-1,2,4-triazol-1-yl)-N'-benzylidenecarbothiohydrazide 2.18 g (0.01 mole) of 1-(5-amino-3-methylthio-1H-1,2,4-triazol-1-yl)-carbothiohydrazide are stirred in 50 ml of methanol, in the presence of 1.52 ml (0.015 mole) of benzaldehyde at room temperature for 24 hours. The reaction mixture is then cooled and the separated crystals are filtered off.

Yield: 2.72 g (93%).
M.p.: 157° to 159° C.

EXAMPLE 24

1-(5-Amino-3-methylthio-1H-1,2,4-triazol-1-yl)-N'-(3,4,5-trimethoxybenzylidene)carbothiohydrazide A mixture of 2.18 g (0.01 mole) of 1-(5-amino-3-methylthio-1H-1,2,4-triazol-1-yl)carbothiohydrazide, 50 ml of methanol and 2.94 g (0.015 mole) of 3,4,5-trimethoxybenzaldehyde is stirred at room temperature for 24 hours. Then it is cooled and the separated crystals are filtered off.

Yield: 3.48 g (91%).
M.p.: 166° to 168° C.

EXAMPLE 25

1-(5-Amino-3-methylthio-1H-1,2,4-triazol-1-yl)-N'-furfurylidenecarbothiohydrazide A mixture of 2.18 g (0.01 mole) of 1-(5-amino-3-methylthio-1H-1,2,4-triazol-1-yl)carbothiohydrazide, 50 ml of methanol, and 1.24 ml (0.015 mole) of furfural is stirred at room temperature for 24 hours. Then the separated crystals are filtered off.

Yield: 2.59 g (92%).
M.p.: 128° to 129° C.

EXAMPLE 26

1-(5-Amino-3-methylthio-1H-1,2,4-triazol-1-yl)-N'-cyclopentylidenecarbothiohydrazide A mixture of 2.18 g (0.01 mole) of 1-(5-amino-3-methylthiol-1H-1,2,4-triazol-1-yl)carbothiohydrazide, 50 ml of methanol and 1.33 ml (0.015 mole) of cyclopentanone is stirred at room temperature for 24 hours. Then the separated crystals are filtered off.

Yield: 2.41 g (89%).
M.p.: 155° to 157° C.

EXAMPLE 27

1-(5-Amino-3-methylthio-1H-1,2,4-triazol-1-yl)-N'-cyclohexylidenecarbothiohydrazide 2.18 g (0.01 mole) of 1-(5-amino-3-methylthio-1H-1,2,4-triazol-1-yl)carbothiohydrazide are stirred in 50 ml of methanol, in the presence of 1.55 ml (0.015 mole) of cyclohexanone at room temperature for 24 hours. The separated crystals are filtered off and recrystallized from methanol.

Yield::L 2.42 g (85%).
M.p.: 128° to 129° C.

EXAMPLE 28

1-(5-Amino-3-morpholino-1H-1,2,4-triazol-1-yl)-N'-cyclopentylidenecarbothiohydrazide A mixture of 2.55 g (0.01 mole) of 1-(5-amino-3-morpholino-1H-1,2,4-triazol-1-yl)carbothiohydrazide, 50 ml of methanol and 1.33 g (0.015 mole) of cyclopentanone is stirred at room temperature for 24 hours. The separated the separated crystals are then filtered off and recrystallized from methanol.

Yield: 2.50 g (81%).
M.p.: 169° to 171° C.

EXAMPLE 29

1-(5-Amino-3-morpholino-1H-1,2,4-triazol-1-yl)-N-methyl-N'-(3,4-methylenedioxybenzylidene)carbothiohydrazide 2.55 g (0.01 mole) of 1-(5-amino-3-morpholino-1H-1,2,4-triazol-1-yl)-N-methyl-carbothiohydrazide are boiled in 25 ml of ethanol, in the presence of 1.65 g (0.011 mole) of piperonal for 2 hours. The reaction mixture is then cooled, the separated crystals are filtered off and recrystallized from isopropanol.

Yield: 2.54 g (71%).
M.p.: 159° to 161° C.

EXAMPLE 30

1-(5-Amino-3-morpholino-1H-1,2,4-triazol-1-yl)-N-methyl-N'-(4-hydroxy-3-methoxybenzylidene)carbothiohydrazide 2.55 g (0.01 mole) of 1-(5-amino-3-morpholino-1H-1,2,4-triazol-1-yl)-N-methyl-carbothiohydrazide are boiled in 25 ml of ethanol, in the presence of 1.67 g (0.011 mole) of vanillin for 3 hours. The reaction mixture is then cooled, the separated crystals are filtered off and recrystallized from methanol.

Yield: 2.87 g (80%).
M.p.: 198° to 200° C.

EXAMPLE 31

1-(5-Amino-3-methylthio-1H-1,2,4-triazol-1-yl)-N-methyl-N'-(3,4-methylenedioxybenzylidene)carbothiohydrazide 2.19 g (001 mole)) of 1-(5-amino-3-methylthio-1H-1,2,4-triazol-1-yl)-N-methyl-carbothiohydrazide are boiled in 20 ml of ethanol, in the presence of 1.65 g (0.011 mole) of piperonal for 5 hours. The reaction mixture is then cooled, the separated crystals are filtered off and recrystallized from dioxane.

Yield: 3.30 g (98%).
M.p.: 212° to 215° C.

EXAMPLE 32

1-(5-Amino-3-methylthio-1H-1,2,4-triazol-1-yl)-N-methyl-N'-(4-hydroxy-3-methoxybenzylidene)carbothiohydrazide 1.1 g (0.005 mole) of 1-(5-amino-3-methylthiol-1H-1,2,4-triazol-1-yl)-N-methyl-carbothiohydrazide are boiled in 20 ml of ethanol, in the presence of 0.76 g (0.005 mole) of vanillin for 4 hours. The reaction mixture is then cooled, the separated crystals are filtered off and recrystallized from methanol.

Yield: 1.02 g (60%).
M.p.: 212° C. to 215° C.

EXAMPLE 33

1-(5-Amino-3-morpholino-1H-1,2,4-triazol-1-yl)-N-methyl-N'-(4-hydroxybenzylidene)carbothiohydrazide 2.55 g (0.01 mole) of a 1-(5-amino-3-morpholino-b 1H-1,2,4-triazol-1-yl)-N-methyl-carbothiohydrazide are boiled in 25 ml of ethanol, in the presence of 1.47 g (0.012 mole) of 4-hydroxybenzaldehyde for 3 hours. The reaction mixture is then cooled, the separated crystals are filtered off and recrystallized from methanol.

Yield: 1.99 g (60%).
M.p.: 136° to 138° C.

EXAMPLE 34

1-(5-Amino-3-methylthio-1H-1,2,4-triazol-1-yl)-N'-[3-(3-dimethylaminopropoxy)-benzylidene]carbothiohydrazide 4.08 g (0.02 mole) of 1-(5-amino-3-methylthio-1H-1,2,4-triazol-1-yl)carbothiohydrazide are boiled in 80 ml of methanol, in the presence of 5.0 g (0.024 mole) of 3-(3-dimethylaminopropoxy)benzaldehyde for 40 minutes. The reaction mixture is then cooled, the separated crystals are filtered off and recrystallized from methanol.

Yield: 7.46 g (95%).
M.p.: 154° to 156° C.

EXAMPLE 35

1-(5-Amino-3-methylthio-1H-1,2,4-triazol-1-yl)-N'-[2-(3-dimethylaminopropoxy)benzylidene]carbothiohydrazide 13.26 g (0.065 mole) of 1-(5-amino-3-methylthio-1-H-1,2,4-triazol-1-yl)carbothiohydrazide are reacted with 13.5 g (0.065 mole) of 2-(3-dimethylaminopropoxy)benzaldehyde in 200 ml of methanol for 30 minutes at room temperature. The separated crystals are filtered off and recrystallized from methanol.

Yield: 23.0 g (90%).
M.p.: 142° to 144° C.

EXAMPLE 36

1-(5-Amino-3-methylthio-1H-1,2,4-triazol-1-yl)-N'-[4-(3-dimethylaminopropoxy)benzylidene]carbothiohydrazide 10.2 g (0.05 mole) of 1-(5-amino-3-methylthio-1-H-1,2,4-triazol-1-yl)carbothiohydrazide are stirred in 140 ml of methanol, in the presence of 11.4 g (0.055 mole) of 4-(3-dimethylaminopropoxy)benzaldehyde for 1 hour at room temperature. The separated crystals are then filtered off and recrystallized from methanol.

Yield: 19.25 g (98%).
M.p.: 160° to 162° C.

EXAMPLE 37

1-(5-Benzylamino-3-morpholino-1H-1,2,4-triazol-1-yl)-N-methyl-N'-(4-chlorobenzylidene)carbothiohydrazide 5.2 g (0.015 mole) of 1-(5-benzylamino-3-morpholino--1H-1,2,4-triazol-1-yl)-N-methyl-carbothiohydrazide are boiled in 15 ml of ethanol, in the presence of 2.8 g (0.02 mole) of 4-chlorobenzaldehyde for 8 hours. The reaction mixture is then cooled, the separated crystals are filtered off and recrystallized from ethanol.

Yield: 5.0 g (92%).
M.p.: 110° to 112° C.

EXAMPLE 38

1-(5-Amino-3-dimethylamino-1H-1,2,4-triazo-1-yl)-N-methyl-N'-(4-methylbenzylidene)carbothiohydrazide 2.15 g (0.01 mole) of 1-(5-amino-3-dimethylamino-1H-1,2,4-triazol-1-yl)-N-methyl-carbothiohydrazide are boiled in 40 ml of ethanol, in the presence of 1.41 g (0.012 mole)) of 4-methylbenzaldehyde for 4 hours. The reaction mixture is then cooled, the separated crystals are filtered off and recrystallized from ethanol.

Yield: 2.0 g (63%)..
M.p.: 171° to 174° C.

EXAMPLE 39

1-(5-Amino-3-diallylamino-1-H-1,2,4-triazol-1-yl)-N-methyl-N'-(4-methylbenzylidene)carbothiohydrazide 1.03 g (0.0038 mole) of 1-(5-amino-3-diallylamino-1H-1,2,4-triazol-1-yl)-N-methyl-carbothiohydrazide are boiled in 15 ml of isopropanol, in the presence of 0.495 ml (0.042 mole) of 4-methylbenzaldehyde for 4 hours. The thus-obtained solution is evaporated to dryness and the residual honey-like product is recrystallized from benzene.

Yield: 0.9 g (62%.
M.p.: 86° to 90° C.

EXAMPLE 40

1-[5-Amino-3-(4-methylpiperazin-1-yl)-1H-1,2,4-triazol-1-yl]-N-methyl-N'-(4-methylbenzylidene)carbothiohydrazide 2.43 g (0.09 mole) of 1-5-amino-3-(4-methylpiperazin-1-yl)-1H-1,2,4-triazol-1-yl]-N-methylcarbothiohydrazide are boiled in 60 ml of ethanol, in the presence of 1.32 g (1.29 ml=0.011 mole) of 4-methylbenzaldehyde for 5 hours. The reaction mixture is then cooled, the separated crystals are filtered off and recrystallized from isopropanol.

Yield: 2.0 g (56%).
M.p.: 175° to 178° C.

EXAMPLE 41

6,8-Dimethyl-2-morpholino-5,6,8,9-tetrahydro[1,2,4]-triazolo-[1,5-d][1,2,4,6]tetrazepine-5(7H)-thione 2.55 g (0.01 mole) of 1-(5-amino-3-morpholino-1H-1,2,4-triazol-1-yl)-N-methyl-carbothiohydrazide are boiled in 25 ml of ethanol, in the presence of 0.84 ml (0.015 mole) of acetaldehyde for 8 hours. The reaction mixture is then cooled, the separated crystals are filtered off and recrystallized from methanol.

Yield: 2.37 g (84%).
M.p.: 226° to 228° C.

EXAMPLE 42

6,8-Dimethyl-2-morpholino-5,6,8,9-tetrahydro[1,2,4]-triazolo[1,5-d][1,2,4,6]tetrazepine-5(7H)-thione 2.55 g (0.01 mole) of 1-(5-amino-3-morpholino-1H-1,2,4-triazol-1-yl)-N-methyl-carbothiohydrazide are stirred in 250 ml of methanol, in the presence of 0.84 g (0.015 mole) of acetaldehyde for 24 hours at room temperature. The reaction mixture is then evaporated in vacuo and the residue is recrystallized from methanol.

Yield: 2.29 g (81%).
M.p.: 226° to 228° C.

EXAMPLE 43

9-Benzyl-6,8-dimethyl-2-morpholino-5,6,8,9-tetrahydro[1,2,4]triazolo[1,5-d][1,2,4,6]tetrazepine-5(7H)-thione 3.45 g (0.01 mole) of 1-(5-benzylamino-3-morpholino-1H-1,2,4-triazol-1-yl)-N-methyl-carbothiohydrazide are boiled in 25 ml of ethanol, in the presence of 0.84 ml (0.015 mole) of acetaldehyde for 8 hours. The reaction mixture is then cooled, the separated crystals are filtered off and recrystallized from ethanol.

Yield: 2.54 g (68%).
M.p.: 193° to 195° C.

EXAMPLE 44

8-Ethyl-6,8-dimethyl-2-morpholino-5,6,8,9-tetrahydro[1,2,4]triazolo[1,5-d][1,2,4,69 tetrazepine-5(7H)-thione 2.55 g (0.01 mole) of 1-(5-amino-3-morpholino-1H-1,2,4-triazol-1-yl)-N-methyl-carbothiohydrazide are boiled in 25 ml of ethanol, in the presence of 0.9 ml (0.015 mole) of 2-butanone for 8 hours. The reaction mixture is then cooled, the separated crystals are filtered off and recrystallized from 2-propanol.

Yield: 1.71 g (55%).
M.p.: 197° to 199° C.

EXAMPLE 45

8-Ethyl-6,8-dimethyl-2-methylthio-5,6,8,9-tetrahydro[1,2,4-triazolo[1,5-d][1,2,4,6]tetrazepine-5(7H-thione 2.18 g (0.01 mole) of 1-(5-amino-3-methylthio-1H-1,2,4-triazol-1-yl)-N-methyl-carbothiohydrazide are boiled in 20 ml of 2-butanone for 8 hours. The reaction mixture is then cooled, the separated crystals are filtered off and recrystallized from methanol.

Yield: 1.42 g (52%).
M.p.: 202° to 205° C.

EXAMPLE 46

6-Methyl-2-methylthio-5,6,8,9,-tetrahydro[1,2,4]-triazolo[1,5-d][1,2,4,6]tetrazepine-5(7H)-thione-8-spiro-1'-cyclopentane 2.18 g (0.01 mole) of 1-(5-amino-3-methylthio-1H-1,2,4-triazol-1-yl)-N-methyl-carbothiohydrazide are stirred in an excess of 5.3 ml (0.06 mole) of cyclopentanone for 5 hours at 140° C. The reaction mixture is then cooled and 25 ml of ethanol are added to it. The mixture is stirred for 1 hour, the separated crystals are filtered off and recrystallized from dioxanel.

Yield: 2.09 g (78%).
M.p.: 202° to 205° C.

EXAMPLE 47

6-Methyl-2-methylthio-5,6,8,9-tetrahydro[1,2,4]-triazolo[1,5-d][1,2,4,6]tetrazepine-5(7H)-thione-8-spiro-1'-cyclohexane 2.18 g (0.01 mole) of 1-(5-amino-3-methylthiol-1H-1,2,4-triazol-1yl)-N-methyl-carbothiohydrazide are stirred in an excess of 6.3 ml (0.06 mole) of cyclohexanone for 5 hours at 140° C. Then it is cooled and 25 ml of ethanol are added to its. The mixture is stirred for 1 hour, the separated crystals are filtered off and recrystallized from dimethylformamide.

Yield: 263 g (93%)).
M.p.: 225° to 227° C.

EXAMPLE 48

6-Methyl-2-morpholino-5,6,8,9-tetrahydro[1,2,4]-triazolo[1,5-d][1,2,4,6]tetrazepine-5(7H)-thione-8-spiro-1'-cyclopentane 2.55 g (0.01 mole) of 1-(5-amino-3-morpholino-1H-1,2,4-triazol-1-yl)-N-methyl-carbothiohydrazide are stirred in an excess of 5.3 ml (0.06 mole) of cyclopentanone for 5 hours at 140° C. the reaction mixture is then cooled and 25 ml of ethanol are added to it. The mixture is stirred for 1 hour, the separated crystals are filtered off and recrystallized from an aqueous ethanol solution.

Yield: 2.00 g (62%).
M.p.: 219° to 222° C.

EXAMPLE 49

6-Methyl-2-morpholino-5,6,8,9-tetrahydro[1,2,4]-triazolo[1,5-d][1,2,4,6]tetrazepine-5(7H)-thione-8spiro-1'-cyclohexane 2.55 g (0.01 mole) of 1-(5-amino-3-morpholino-1H-1,2,4-triazol-1-yl)-N-methyl-carbothiohydrazide are stirred in an excess of 6.3 ml (0.06 mole) of cyclohexanone at 140° C. for 5 hours. Then it is cooled and 25 ml of ethanol are added to it. The mixture is stirred for 1 hour, the separated crystals are filtered off and recrystallized from an aqueous dimethylformamide solution.

Yield: 2.60 g (77%).
M.p.: 223° to 225° C.

EXAMPLE 50

6-Methyl-2-morpholino-5,6,8,9-tetrahydro[1,2,4]-triazolo[1,5-d][1,2,4,6]tetrazepine-5(7H)-thione-8-spiro-1'-cyclohexane 2.55 g (0.01 mole) of 1-(5-amino-3-morpholino-1H-1,2,4-triazol-1-yl)-N-methyl-carbothiohydrazide are stirred in 30 ml of dimethylformamide, in the presence of 3.15 ml (0.03 mole) of cyclohexanone at 80° C. for 8 hours. 30 ml of water are added to the reaction mixture which is then stirred for 1 hour, the separated crystals are filtered off and recrystallized from an aqueous dimethylformamide solution.

Yield: 2.29 g (68%).
M.p.: 223° to 225° C.

EXAMPLE 51

6-methyl-2-morpholino-5,6,8,9-tetrahydro[1,2,4]-triazolo[1,5-d][1,2,4,6]tetrazepine-5(7H)-thione-8-spiro-1'-cycloheptane 2.55 g (0.01 mole) of 1-(5-amino-3-morpholino-1H-1,2,4-triazol-1-yl)-N-methyl-carbothiohydrazide are boiled in 25 ml of ethanol, in the presence of 1.68 ml (0.015 mole) of cycloheptanone for 8 hours. The reaction mixture is then cooled, the separated crystals are filtered off and recrystallized from ethanol.

Yield: 2.28 g (65 %).
M.p.: 209° to 211° C.

EXAMPLE 52

6-Methyl-2-morpholino-5,6,8,9-tetrahydro[1,2,4]-triazolo[1,5-d][1,2,4,6]tetrazepine-5(7H)-thione-8-spiro-1'-cyclooctane 2.55 g (0.01 mole) of 1-(5-amino-3-morpholino-1H-1,2,4-triazol-1-yl)-N-methyl-carbothiohydrazide are boiled in 25 ml of ethanol, in the presence of 1.98 ml (0.015 mole) of cyclooctanone for 8 hours. The reaction mixture is then cooled, the separated crystals are filtered off and recrystallized from ethanol.

Yield: 2.59 g (71%).
M.p.: 204° to 1206° C.

EXAMPLE 53

6-Methyl-2-morpholino-5,6,8,9-tetrahydro-1,2,4-triazolo[1,5-d][1,2,4,6]tetrazepine-5(7H)-thione-8-spiro-1'-cyclododecane 2.55 g (0.01 mole) of 1-(5-amino-3-morpholino-1H-1,2,4-triazol-1-yl)-N-methyl-carbothiohydrazide are boiled in 25 ml of ethanol, in the presence of 2.73 g (0.015 mole) of cyclododecanone for 8 hours. The reaction mixture is then cooled, the separated crystals are filtered off and recrystallized from ethanol.

Yield: 2.66 g (63%).
M.p.: 203° to 205° C.

EXAMPLE 54

6-Methyl-2-morpholino-5,6,8,9-tetrahydro[1,2,4]-triazolo[1,5-d][1,2,4,6]tetrazepine-5(7H)-thione-8-spiro-4'-(N-benzylpiperidine)

2.55 g (0.01 mole) of 1-(5-amino-3-morpholino-1H-1,2,4-triazol-1-yl)-N-methyl-carbothiohydrazide are boiled in 25 ml of ethanol, in the presence of 2.78 g (0.015 mole) of N-benzyl-4-piperidone for 8 hours. The reaction mixture is then cooled, the separated crystals are filtered off and recrystallized from methanol.
Yield: 2.48 g (58%).
M.p.: 227° to 229° C.

EXAMPLE 55

6-Methyl-2-morpholino-5,6,8,9-tetrahydro[1,2,4]-triazolo[1,5-d][1,2,4,6]tetrazepine-5(7H)-thione-8-spiro-3'-thiacyclohexane 2.55 g (0.01 mole) of 1-(5-amino-3-morpholino-1H-1,2,4-triazol-1-yl)-N-methyl-carbothiohydrazide are boiled in 25 ml of methanol, in the presence of 1.74 g (0.015 mole) of 3-thiacyclohexanone for 8 hours. The reaction mixture is then cooled, the separated crystals are filtered off and recrystallized from methanol.
Yield: 1.74 g (49%).
M.p.: 226° to 228° C.

EXAMPLE 56

6,8-Dimethyl-8-methoxycarbonyl-methyl-2-morpholino-5,6,8,9-tetrahydro[1,2,4]triazolo[1,5-d][1,2,4,6]-tetrazepine-5(7H)-thione 2.55 (0.01 mole) of 1-(5-amino-3morpholino-1H-1,2,4-triazol-1-yl)-N-methyl-carbothiohydrazide are boiled in 25 ml of ethanol, in the presence of 1.74 g (0.015 mole) of methylacetoacetate for 8 hours. The reaction mixture is then cooled, the separated crystals are filtered off and recrystallized from 2-propanol.
Yield: 2.27 g (64%).
M.p.: 2101° to 203° C.

EXAMPLE 57

6,8-Dimethyl-8-methoxycarbonyl-methyl-2-methylthio-5,6,8,9tetrahydro[1,2,4]triazolo[1,5-d][1,2,4,6]-tetrazepine-5(7H)-thione 2.18 g (0.01 mole) of 1-(5-amino-3-methylthiol-1H-1,2,4-triazol-1-yl)-N-methyl-carbothiohydrazide are boiled in 25 ml of ethanol, in the presence of 1.74 ml (0.015 mole) of methylacetoacetate for 8 hours. The reaction mixture is then cooled, the separated crystals are filtered off and recrystallized from acetonitirile.
Yield: 2.34 g (74%).
M.p.: 198° to 200° C.

EXAMPLE 58

6,8-Dimethyl-8-(ethoxycarbonyl-ethyl)-2-morpholino-5,6,8,9-tetrahydro[1,2,4]triazolo[1,5-d][1,2,4,6]-tetrazepine-5(7H)-thione 2.55 g (0.01 mole) of 1-(5amino-3-morpholino-1H-1,2,4-triazol-1-yl)-N-methyl-carbothiohydrazide are boiled in 25 ml of ethanol, in the presence of 2.13 ml (0015 mole) of ethyl levulinate for 8 hours. The reaction mixture is then cooled, the separated crystals are filtered off and recrystallized from 2-propanol.
Yield: 2.25 g (61%).
M.p.: 176° to 178° C.

EXAMPLE 59

1-(5-Amino-3-morpholino-1H-1,2,4-triazol-1-yl)-N-methyl-N'-(2,6-dichlorobenzylidene)carbothiohydrazide 2.55 g (0.01 mole) of 1-(5-amino-3-morpholino-1H-1,2,4-triazol-1-yl)-N-methyl-carbothiohydrazide are boiled in 25 ml of ethanol, in the presence of 0.84 ml (0.015 mole) of 2,6-dichlorobenzaldehyde for 8 hours. The reaction mixture is then cooled, the separated crystals are filtered off and recrystallized from 2-propanol.
Yield: 3.44 g (69%).
M.p.: 152° to 154° C.

EXAMPLE 60

8-(2,6-Dichlorophenyl)-6-methyl-2-morpholino-5,6,8,9-tetrahydro[1,2,4]triazolo[1,5-d][1,2,4,6]-tetrazepine-5(7H)-thione 3.44 g (0.01 mole) of 1-(5-amino-3-morpholino-1H-1,2,4-triazol-1-yl)-N-methyl-N'-(2,6-dichlorobenzylidene) carbothiohydrazide prepared as described in Example 59 are boiled in a 1:1 mixture of dimethylformamide and water for 30 minutes. The reaction mixture is then cooled, the separated crystals are filtered off and recrystallized from an aqueous dimethylformamide solution.
Yield: 2.75 g (80%).
M.p.: 208° to 210° C.

EXAMPLE 61

8-(2,6-Dichlorophenyl)-6-methyl-2-morpholino-5,6,8,9-tetrahydro[1,2,4]triazolo[1,5-d][1,2,4,60-tetrazepine-5(7H)-thione 3.44 g of 1-(5-amino-3-morpholino-1H-1,2,4-triazol-1-yl)N-methyl-N'-(2,6-dichlorobenzylidene)-carbothiohydrazide prepared according to Example 59 are stirred in 100 ml of acetic acid for 8 hours at 80° C. The separated crystals are filtered off and recrystallized from an aqueous dimethylformamide solution.
Yield: 2.06 g (60%).
M.p.: 208° to 210° C.

EXAMPLE 62

8-Phenyl-6-methyl-2-morpholino-5,6,8,9-tetrahydro-∂1,2,4]triazolo[1,5-d][1,2,4,6]tetrazepine-5(7H)-thione 2.55 g (0.01 mole) of 1-(5-amino-3-morpholino-1H-1,2,4-triazol-1-yl)-N-methyl-carbothiohydrazide are boiled in 25 ml of ethanol, in the presence of 1.22 ml (0.012 mole) of benzaldehyde for 8 hours. The reaction mixture is then cooled, the separated crystals are filtered off and recrystallized from 2-propanol. According to TLC analysis the 2.8 g of crystalline product thus obtained are 1-(5-amino-3-morpholino-1H-1,2,4-triazol-1-yl)-N-methyl-N'-benzylidene-carbothiohydrazide contaminated with a slight amount of 8-phenyl-6-methyl-2-morpholino-5,6,8,9-tetrahydro[1,2,4]triazolo[1,5-d][1,2,4,6]tetrazepine-5(7H)-thione. TLC investigations were made on silica gel plates (Merck Kieselgel GF$_{254}$). The spots were developed with a 9:1 mixture of chloroform and methanol. R$_{f(Ia)}$=0.5, R$_{f(Ib)}$=0.65.

The thus-obtained crystals are boiled in 30 ml of a 1:1 mixture of dimethylformamide and water. The mixture is then cooled, the separated crystals are filtered off and recrystallized from an aqueous dimethylformamide solution.

Yield: 2.16 g (63%).
M.p.: 212° to 214° C.

EXAMPLE 63

9-Benzyl-8-(4-chlorophenyl)-6-methyl-2-morpholino-5,6,8,9-tetrahydro[1,2,4]triazolo[1,5-d][1,2,4,6]-tetrazepine-5(7H)-thione A suspension of 0.75 g (0.00016 mole) of 1-(5-benzylamino-3-morpholino-1-H-1,2,4-triazol-1-yl)-N-methyl-N'-(4-chlorobenzylidene)carbothiohydrazide in a 8 ml of acetic acid and 5.5 ml of water is stirred at room temperature for 24 hours. The reaction is followed by TLC on silica gel plates (merck Kieselgel GF$_{254}$). The spots were developed with a 9:1 mixture of chloroform and methanol. R$_{f(Ia)}$=0.85, R$_{f(Ib)}$=0.45. The thus-obtained product is filtered off and washed with a slight amount of water.
Yield: 0.70 g (93%.
M.p.: 179° to 183° C.

EXAMPLE 64

6,8-Dimethyl-9-(4-chlorobenzyl)-2-morpholino-5,6,8,9-tetrahydro[1,2,4]triazolo[1,5-d][1,2,4,6]-tetrazepine-5(7H)-thione 1.15 g (0.003 mole) of 1-[5-(4-chlorobenzylamino)-3-morpholino-1H-1,2,4-triazol-1-yl]-N-methyl-carbothiohydrazide are boiled in 20 ml of ethanol, in the presence of 1.0 ml of acetaldehyde for 8 hours. The solution is evaporated in vacuo. Isopropanol is added to it, the separated crystals are filtered off and recrystallized from isopropanol.
Yield: 0.62 g (51%).
M.p.: 202° to 204° C.

EXAMPLE 65

6-Methyl-2-methylthiol-5,6,8,9-tetrahydro[1,2,4]-triazolo[1,5-d][1,2,4,6]tetrazepine-5(7H)-thione-8-spiro-1'-cyclopentane 2.19 g (0.01 mole) of 1-(5-amino-3-methylthio-1H-1,2,4-triazol-1-yl)-N-methyl-carbothiohydrazide are boiled in 20 ml of ethanol, in the presence of 1.68 g (0.02 mole) of cyclopentanone for 24 hours. Then it is cooled, the separated crystals are filtered off and recrystallized from dioxane.
Yield: 2.11 g (74%).
M.p.: 186° to 190° C.

EXAMPLE 66

6-Methyl-2-methylthio-5,6,8,9-tetrahydro[1,2,4]-triazolo[1,5-d][1,2,4,6]tetrazepine-5(7H)-thione-8-spiro-1'-cyclohexane 2.18 g (0.01 mole) of 1-(5-amino-3-methylthio-1H-1,2,4-triazol-1-yl)-N-methyl-carbothiohydrazide are boiled in 20 ml of ethanol, in the presence of 1.46 g (1.55 ml, 0.015 mole) of cyclohexanone for 5 hours. The mixture is then cooled, the separated crystals are filtered off and washed with ethanol.
Yield: 2.8 g (94%).
M.p.: 207 to 210° C.

EXAMPLE 67

1-(5-Amino-3-morpholino-1H-1,2,4-triazol-1-yl)-N-methyl-carbothiohdrazide

[starting compound of the general formula (II)]

25.7 g (0.1 mole) of methyl-(5-amino-3-morpholino-1H-1,2,4-triazol-1-yl)carbothiohydrazide are stirred in 150 ml of methanol, in the presence of 6.9 ml (0.13 mole) of methylhydrazine at room temperature for 4 hours. The separated crystals are filtered off and recrystallized from benzene.
Yield: 15.0 g (59%).
M.p.: 144° to 146° C.

EXAMPLE 68

Tablets having the following composition are prepared by known methods of the pharmaceutical industry:

| Component | Amount, mg/tablet |
| --- | --- |
| 1-(5-Amino-3-morpholino-1H-1,2,4-triazol-1-yl)-N-methyl-N'-(2,6-dichlorobenzylidene)-carbothiohydrazide | 250 |
| Lactose | 61.8 |
| Potato starch | 43.2 |
| Polyvinylpyrrolidone | 22.5 |
| Stearic acid | 9.0 |
| Talc | 13.5 |
| Total weight: | 400.0 mg |

EXAMPLE 69

Ointments having the following composition are prepared by known methods of the pharmaceutical industry:

| Component | Amount (mg) |
| --- | --- |
| 1-(5-Amino-3-morpholino-1H-1,2,4-triazol-1-yl)-N-methyl-N'-(2,6-dichlorobenzylidene)-carbothiohydrazide | 500 |
| Unguentum hydrophilicum nonbonicum | 1000 |

The active ingredient is in the outer phase of the ointment, in dissolved state.

EXAMPLE 70

Suppositories having the following composition are prepared by known methods of the pharmaceutical industry:

| Component | Amount, mg/suppository |
| --- | --- |
| 1-(5-Amino-3-morpholino-1H-1,2,4-triazol-1-yl)-N-methyl-N'-(2,6-dichlorobenzylidene)-carbothiohydrazide | 100 |
| Lecithin | 48 |
| Cera alba | 96 |
| Cocoa butter | 1870 |
| Distilleld water | 386 |
| Total weight: | 2500 mg |

EXAMPLE 71

Capsules having the following composition are prepared by known methods of the pharmaceutical industry:

| Component | Amount, mg/capsule |
| --- | --- |
| 1-(5-Amino-3-morpholino-1H-1,2,4-triazol-1-yl)-N-methyl-N'-(2,6-dichlorobenzylidene)-carbothiohydrazide | 100 |

| Component | Amount, mg/capsule |
|---|---|
| Lactose | 59.5 |
| Potato starch | 5 |
| Magnesium stearate | 0.5 |
| Total weight: | 180 mg |

EXAMPLE 72

Tablets having the following composition are prepared by known methods of the pharmaceutical industry:

| Component | Amount, mg/tablet |
|---|---|
| 6-Methyl-2-morpholino-5,6,8,9-tetrahydro[1,2,4]triazolo[1,5-d]-[1,2,4,6]-tetrazepine-5(7H)-thione-8-spiro-4'-(N-benzylpiperidine) | 100 |
| Lactose | 41.2 |
| Potato starch | 28.8 |
| Polyvinylpyrrolidone | 15.0 |
| Stearic acid | 6.0 |
| Talc | 9.0 |
| Total weight: | 200.0 mg |

EXAMPLE 73

Ointments having the following composition are prepared by known methods of the pharmaceutical industry:

| Component | Amount (mg) |
|---|---|
| 6-Methyl-2-morpholino-5,6,8,9-tetrahydro[1,2,4]triazolo[1,5-d]-[1,2,4,6]-tetrazepine-5(7H)-thione-8-spiro-4'-(N-benzylpiperidine) | 500 |
| Unguentum hydrophilicum nonbonicum | 1000 |

The active ingredient is in the outer phase of the ointment, in dissolved state.

EXAMPLE 74

Suppositories having the following composition are prepared by known methods of the pharmaceutical industry:

| Component | Amount, mg/suppository |
|---|---|
| 6-Methyl-2-morpholino-5,6,8,9-tetrahydro[1,2,4]triazolo[1,5-d]-[1,2,4,6]-tetrazepine-5(7H)-thione-8-spiro-4'-(N-benzylpiperidine) | 100 |
| Lecithin | 48 |
| Cera alba | 96 |
| Cocoa butter | 1870 |
| Distilled water | 386 |
| Total weight: | 2500 mg |

EXAMPLE 75

Capsules having the following composition are prepared by known methods of the pharmaceutical industry:

| Component | Amount (mg) |
|---|---|
| 6-Methyl-2-morpholino-5,6,8,9-tetrahydro[1,2,4]triazolo[1,5-d]- | 100 |
| [1,2,4,6]-tetrazepine-5(7H)-thione-8-spiro-4'-(N-benzylpiperidine) | |
| Lactose | 59.5 |
| Potato starch | 5 |
| Magnesium stearate | 0.5 |
| Total weight: | 180.0 mg |

What we claim is:

1. Triazolo derivatives of the general formulae (Ia) and (Ib), mixtures and pharmaceutically acceptable acid addition salts thereof,

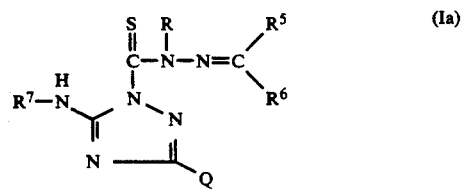

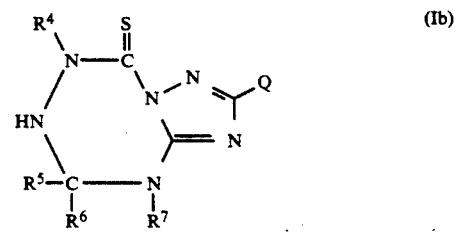

wherein
Q represents morpholino or piperazino group optionally bearing one $C_{1-4}$ alkyl substituent; or a group of the formula $SR^1$, wherein
$R^1$ stands for $C_{1-4}$ alkyl or Q represents the formula NR $R^3$, wherein
$R^2$ and $R^3$ each represent $C_{1-4}$ alkyl, $C_{2-6}$ alkenyl;
$R^4$ and $R^7$ each represent hydrogen, $C_{1-4}$ alkyl or phenyl($C_{1-4}$ alkyl) optionally bearing one halogen substituent;
$R^5$ and $R^6$ each stand for $C_{1-4}$ alkyl optionally substituted by a $C_{1-4}$ alkoxycarbonyl group; a furyl or piperidinyl group or a phenyl group optionally bearing one or more halogen, hydroxyl, cyano, nitro, di-($C_{1-4}$ alkyl)-amino or $C_{1-4}$ alkoxy substituent(s) which latter may carry a di-($C_{1-4}$ alkyl)-amino group; furthermore one of $R^5$ and $R^6$ may represent hydrogen, or
$R^5$ and $R^6$ together stand for $C_{4-15}$ alkylene, or together with the adjacent carbon atom they are attached to form a six-membered heterocyclic group containing sulfur or nitrogen as hetero atom which latter carries a phenyl-($C_{1-4}$ alkyl) substituent.

2. Compounds of the general formulae (Ia) and (Ib), wherein Q represents morpholino, $R^4$ stands for $C_{1-4}$ alkyl, $R^5$ and $R^6$ denote phenyl bearing one or more halogen substituent(s) or together stand for $C_{4-15}$ alkylene, and pharmaceutically acceptable acid addition salts thereof.

3. The triazolo derivatives according to claim 1, wherein said derivatives are selected form the group consisting of 1-(5-amino-3-morpholino-1H-1,2,4-triazol-1-yl)-N-methyl-N'-(2,6-dichlorobenzylidene)carbothiohydrazide; 6-methyl-2-morpholino-5,6,8,9-tetrahydro(1,2,4)triazolo-(1,5-d)-(1,2,4,6)tetrazepin-5(7H)- thione-8-spiro-1'-cyclodecane; 6-methyl-2-morpholino-5,6,8,9-tetrahydro(1,2,4)triazolo-(1,5-d)-(1,2,4,6)tetrazepin-5(7H)-thione-8-spiro-1'-cyclopentane; and pharmaceutically acceptable acid addition salts thereof.

4. Pharmaceutical compositions comprising as active ingredient at least one compound of the general formula (Ia) or (Ib) or a pharmaceutically acceptable salt thereof in admixture with suitable inert solid or liquid pharmaceutical carriers.

5. Method of antianginal and/or tranquillant/sedative treatment, which comprises administering to a patient an effective amount of a compound of the general formula (Ia) and/or (Ib) or a pharmaceutically acceptable salt thereof.

* * * * *